(12) United States Patent
de Luca

(10) Patent No.: US 7,674,453 B2
(45) Date of Patent: Mar. 9, 2010

(54) TUMOR NECROSIS FACTOR COMBINED WITH INTERFERON IN DEMYELINATING DISEASES

(75) Inventor: Giampiero de Luca, Conches-Geneva (CH)

(73) Assignee: Ares Trading SA, Aubonne (CH)

( * ) Notice: Subject to any disclaimer, the term of this patent is extended or adjusted under 35 U.S.C. 154(b) by 0 days.

(21) Appl. No.: 10/503,525

(22) PCT Filed: Jan. 29, 2003

(86) PCT No.: PCT/EP03/50006

§ 371 (c)(1),
(2), (4) Date: Feb. 18, 2005

(87) PCT Pub. No.: WO03/066165

PCT Pub. Date: Aug. 14, 2003

(65) Prior Publication Data

US 2005/0142100 A1    Jun. 30, 2005

(30) Foreign Application Priority Data

Feb. 6, 2002    (EP)    ................ 02100110

(51) Int. Cl.
*A61K 45/00* (2006.01)
*A61K 38/21* (2006.01)
*A61K 39/00* (2006.01)
*A61K 38/16* (2006.01)

(52) U.S. Cl. .............. 424/85.1; 424/85.4; 424/85.6; 424/178.1; 514/2; 514/12

(58) Field of Classification Search ............. None
See application file for complete search history.

(56) References Cited

U.S. PATENT DOCUMENTS

| 4,791,101 | A | | 12/1988 | Adolf |
| 4,792,101 | A | | 12/1988 | Van Bogaert |
| 5,098,702 | A | * | 3/1992 | Zimmerman et al. ........ 424/85.1 |
| 6,013,253 | A | * | 1/2000 | Martin et al. ............... 424/85.7 |
| 6,083,534 | A | * | 7/2000 | Wallach et al. ............. 424/484 |
| 6,225,300 | B1 | * | 5/2001 | Boe et al. ................... 514/171 |
| 7,091,321 | B2 | * | 8/2006 | Gillies et al. .............. 530/387.3 |

FOREIGN PATENT DOCUMENTS

| EP | 0248516 B1 | 12/1987 |
| EP | 0880970 A1 | 12/1998 |

(Continued)

OTHER PUBLICATIONS

Barrera et al., Semin Arthritis Rheum. Feb. 1996;25(4):234-53.*

(Continued)

*Primary Examiner*—Cherie M Woodward
(74) *Attorney, Agent, or Firm*—Saliwanchik, Lloyd & Saliwanchik

(57) ABSTRACT

The invention relates to the use of an agent having, stimulating or maintaining tumor necrosis factor (TNF) activity, together with an interferon (IFN) for treating and/or preventing demyelinating diseases, in particular multiple sclerosis (MS). The use of a combination of a TNF or a tumor necrosis factor binding protein in combination with an interferon for treating and/or preventing demyelinating diseases is preferred.

14 Claims, 9 Drawing Sheets

FOREIGN PATENT DOCUMENTS

| | | |
|---|---|---|
| EP | 0512528 | 9/1999 |
| WO | WO 92/07578 A1 | 5/1992 |
| WO | WO 96/03141 | 2/1996 |
| WO | WO 97/03686 A1 | 2/1997 |
| WO | WO 99/21591 A1 | 5/1999 |
| WO | WO 00/06577 A1 | 2/2000 |
| WO | WO 0023472 A2 * | 4/2000 |
| WO | WO 00/66158 A2 | 11/2000 |
| WO | WO 01/41782 A2 | 6/2001 |
| WO | WO 01/60392 A1 | 8/2001 |
| WO | WO 01/61017 A2 | 8/2001 |

OTHER PUBLICATIONS

Paya et al., (Int Immunol. 1990;2(9):909-13).*
Sibson et al., (Brain. 2002;125:2446-2459).*
Sicotte et al., (Neurology. Nov. 27, 2001;57(10):1885-8).*
Becker et al., Am J Health Syst Pharm. Sep. 15, 1995;52(18):1985-2000, Abstract Only.*
Inoue et al. (Intl Immunol. 1996;8(7):1001-1008) (provided by Applicant in Response filed Feb. 19, 2009).*
Klinkert, W.E.F. et al. "TNF-α receptor fusion protein prevents experimental auto-immune encephalomyelitis and demyelination in Lewis rats: an overview" *Journal of Neuroimmunology*, 1997, pp. 163-168, vol. 72.
Martin, D. et al. "Cytokines as Therapeutic Agents in Neurological Disorders" Cytokines as Therapeutic Agents in Neurological Disorders, In *Cytokines in the Nervous System*, 1996, Chapter 9, pp. 163-177.
Hoogenboom, H.R. et al. "Construction and expression of antibody-tumor necrosis factor fusion proteins" *Mol. Immunol.*, 1991, 28:1027-1037, Only Abstract Considered.
Narhi, L.O. et at. "The limited proteolysis of tumor necrosis factor-alpha" *J. Protein Chem.*, 1989, 8:669-677, Only Abstract Considered.

* cited by examiner

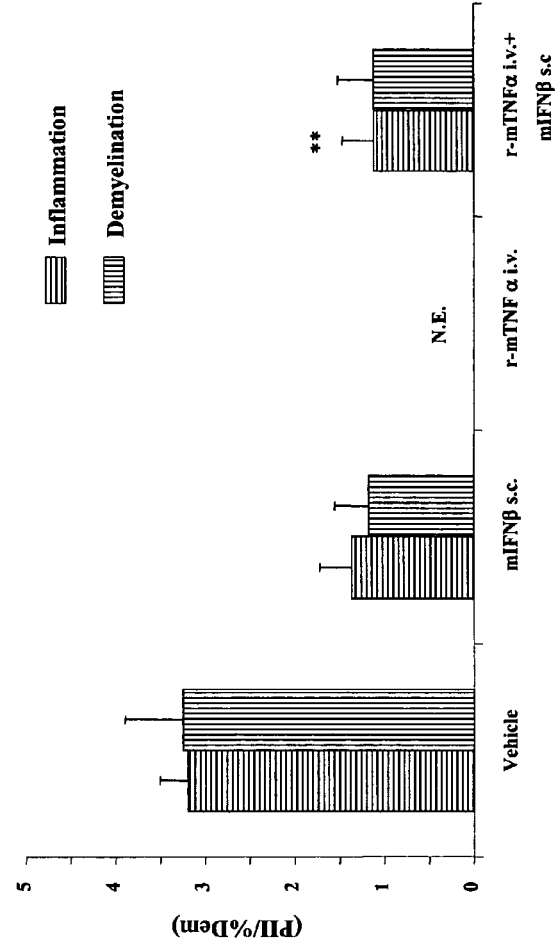

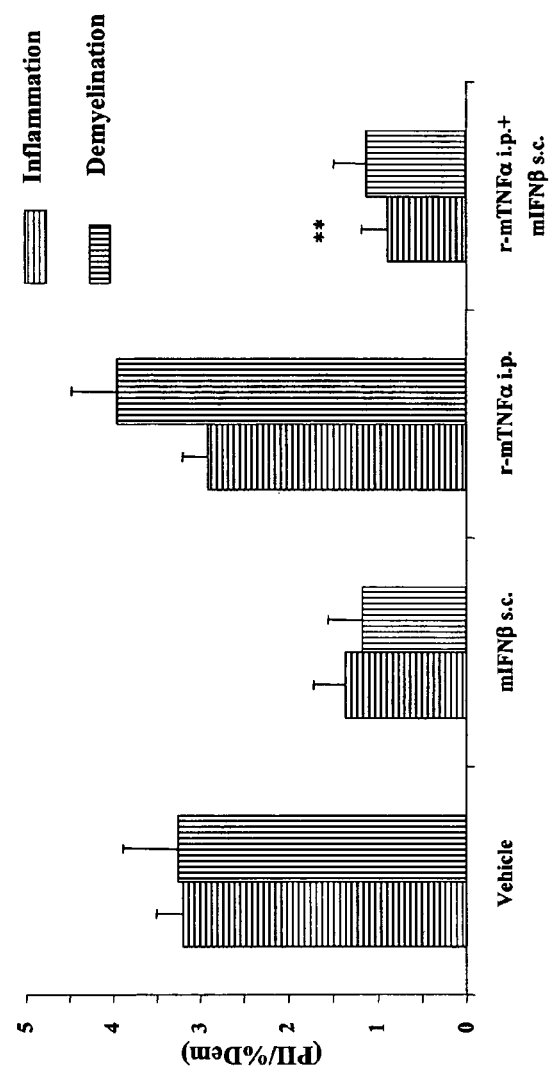

SEQUENCE LISTING

```
<160> NUMBER OF SEQ ID NOS: 1

<210> SEQ ID NO 1
<211> LENGTH: 13
<212> TYPE: PRT
<213> ORGANISM: Artificial sequence
<220> FEATURE:
<223> OTHER INFORMATION: amino acid linker sequence

<400> SEQUENCE: 1

Glu Phe Gly Ala Gly Leu Val Leu Gly Gly Gln Phe Met
1               5                   10
```

TUMOR NECROSIS FACTOR COMBINED WITH INTERFERON IN DEMYELINATING DISEASES

CROSS-REFERENCE TO RELATED APPLICATION

This application is the U.S. national stage application of International Patent Application No. PCT/EP03/50006, filed Jan. 29, 2003, which claims the benefit of European Patent Application Number 02100110.2, filed Feb. 6, 2002.

FIELD OF THE INVENTION

The present invention is in the field of neurological disorders. It relates to the use of an agent having, stimulating or maintaining tumor necrosis factor (TNF) activity in combination with an interferon (IFN) for the manufacture of a medicament for treatment and/or prevention of a demyelinating disease. In particular, it relates to the use of a combination of TNF-alpha and IFN-beta for treatment and/or prevention of a demyelinating disease, such as multiple sclerosis (MS). The invention further relates to the use of a tumor necrosis factor binding protein (TBP) in combination with an interferon (IFN) for the manufacture of a medicament for treatment and/or prevention of a demyelinating disease, in particular multiple sclerosis (MS).

BACKGROUND OF THE INVENTION

Demyelinating diseases are disorders concerning the myelin sheaths of the nervous system. Myelin sheaths, which cover many nerve fibers, are composed of lipoprotein layers formed in early life. Myelin is formed by the oligodendroglia in the CNS and promote transmission of a neural impulse along an axon.

Many congenital metabolic disorders (e.g. phenylketonuria and other aminoacidurias; Tay-Sachs, Niemann-Pick, and Gaucher's diseases; Hurler's syndrome; Krabbe's disease and other leukodystrophies) affect the developing myelin sheath, mainly in the CNS. Unless the biochemical defect can be corrected or compensated for, permanent, often widespread, neurological deficits result.

Demyelination in later life is a feature of many neurological disorders; it can result from damage to nerves or myelin due to local injury, ischemia, toxic agents, or metabolic disorders. Extensive myelin loss is usually followed by axonal degeneration and often by cell body degeneration, both of which may be irreversible. However, remyelination occurs in many instances, and repair, regeneration, and complete recovery of neural function can be rapid. Recovery often occurs after the segmental demyelination that characterizes many peripheral neuropathies; this process may account for the exacerbations and remissions of multiple sclerosis (MS). Central demyelination (i.e. of the spinal cord, brain, or optic nerves) is the predominant finding in the primary demyelinating diseases, whose etiology is unknown. The most well known demyelinating disease is MS (see below).

Further demyelinating diseases comprise:

Acute disseminated encephalomyelitis, which is characterized by perivascular CNS demyelination, and which can occur spontaneously but usually follows a viral infection or viral vaccination;

Acute inflammatory peripheral neuropathies that follow a viral vaccination or the Guillain-Barré syndrome, they affect only peripheral structures;

Adrenoleukodystrophy and adrenomyeloneuropathy, which are rare X-linked recessive metabolic disorders characterized by adrenal gland dysfunction and widespread demyelination of the nervous system;

Leber's hereditary optic atrophy and related mitochondrial disorders, which are characterized primarily by bilateral loss of central vision, and which can resemble the optic neuritis in MS; and HTLV-associated myelopathy, a slowly progressive spinal cord disease associated with infection by the human T-cell lymphotrophic virus, that is characterized by spastic weakness of both legs.

Multiple sclerosis (MS) is a slowly progressive CNS disease characterized by disseminated patches of demyelination in the brain and spinal cord, resulting in multiple and varied neurological symptoms and signs, usually with remissions and exacerbation (see The Merck Manual Home Edition, www.merck.com).

The cause is unknown but an immunological abnormality is suspected, with few clues presently indicating a specific mechanism. Postulated causes include infection by a slow or latent virus, and myelinolysis by enzymes. IgG is usually elevated in the CSF, and elevated titers have been associated with a variety of viruses, including measles. The significance of these findings and of reported associations with HLA allotypes and altered number of T cells is unclear, and the evidence somewhat conflicting. An increased family incidence suggests genetic susceptibility; women are somewhat more often affected than men. Environmental factors seem to be present. Although age at onset generally is from 20 to 40 years, MS has been linked to the geographic area where a patient's first 15 years are spent. Relocation after age 15 does not alter the risk.

Plaques or islands of demyelination with destruction of oligodendroglia and perivascular inflammation are disseminated through the CNS, primarily in the white matter, with a predilection for the lateral ad posterior columns (especially in the cervical and dorsal regions), the optic nerves, and periventricular areas. Tracts in the midbrain, pons, and cerebellum also are affected, and gray matter in both cerebrum and cord may be affected.

Cell bodies and axons are usually preserved, especially in early lesions. Later, axons may be destroyed, especially in the long tracts, and a fibrous gliosis gives the tracts their "sclerotic" appearance. Both early and late lesions may be found simultaneously. Chemical changes in lipid and protein constituents of myelin have been demonstrated in and around the plaques.

The disease is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g., partial blindness and pain in one eye (retrobulbar optic neuritis), dimness of vision, or scotomas. Other common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized.

The course is highly varied, unpredictable, and, in most patients, remittent. Life span is probably not shortened except in the most severe cases. At first, months or years of remission may separate episodes, especially when the disease begins with retrobulbar optic neuritis. Remissions can last >10 years.

However, some patients have frequent attacks and are rapidly incapacitated; for a few, particularly for male patients with onset in middle age, the course can be rapidly progressive. Exposure to excess heat from fever or the environment sometimes worsens symptoms.

Diagnosis is indirect, by deduction from clinical and laboratory features. MRI, the most sensitive diagnostic imaging technique, may show plaques. Gadolinium-contrast enhancement can distinguish areas of active inflammation from older brain plaques. MS lesions may also be visible on contrast-enhanced CT scans, in which sensitivity may be increased by giving twice the iodine dose and delaying scanning (double-dose delayed CT scan).

CSF is abnormal in the majority of patients. IgG may be >13%, and lymphocytes and protein content may be slightly increased. Oligoclonal bands, which indicate IgG synthesis within the blood-brain barrier, may be detected by agarose electrophoresis of CSF in up to 90% of patients with MS, but absence of these bands does not rule out MS. IgG levels correlate with disease severity. Myelin basic protein may be elevated during active demyelination.

Spontaneous remissions and fluctuating symptoms make treatments difficult to evaluate. Corticosteroids are the main form of therapy. They may shorten the symptomatic period during attacks, although they may not affect eventual long-term disability. Patients presenting with acute severe optic neuritis may delay the onset of MS by using high-dose IV corticosteroids.

Immunosuppressive drugs (methotrexate, azathioprine, cyclophosphamide, cladribine) are generally used for more severe progressive forms. Immunomodulatory therapy with interferon-β reduces the frequency of relapses in MS. Other promising treatments still under investigation include other interferons, oral myelin, and glatiramer to help keep the body from attacking its own myelin. Glatiramer is a synthetic co-polymer with similarities to myelin basic protein and is administered by daily subcutaneous injection. Its main action is thought to be suppression of the immune response against myelin to promote immune tolerance (Clegg and Bryant, 2001).

Interferons are cytokines, i.e. soluble proteins that transmit messages between cells and play an essential role in the immune system by helping to destroy micro-organisms that cause infection and repairing any resulting damage. Interferons are naturally secreted by infected cells and were first identified in 1957. Their name is derived from the fact that they "interfere" with viral replication and production.

Interferons exhibit both antiviral and antiproliferative activity. On the basis of biochemical and immunological properties, the naturally-occurring human interferons are grouped into three major classes: interferon-alpha (leukocyte), interferon-beta (fibroblast) and interferon-gamma (immune). Alpha-interferon is currently approved in the United States and other countries for the treatment of hairy cell leukemia, venereal warts, Kaposi's Sarcoma (a cancer commonly afflicting patients suffering from Acquired Immune Deficiency Syndrome (AIDS)), and chronic non-A, non-B hepatitis.

Further, interferons (IFNs) are glycoproteins produced by the body in response to a viral infection. They inhibit the multiplication of viruses in protected cells. Consisting of a lower molecular weight protein, IFNs are remarkably non specific in their action, i.e. IFN induced by one virus is effective against a broad range of other viruses. They are however species-specific, i.e. IFN produced by one species will only stimulate antiviral activity in cells of the same or a closely related species. IFNs were the first group of cytokines to be exploited for their potential anti-tumor and antiviral activities.

The three major IFNs are referred to as IFN-α, IFN-β and IFN-γ. Such main kinds of IFNs were initially classified according to their cells of origin (leukocyte, fibroblast or T cell). However, it became clear that several types may be produced by one cell. Hence leukocyte IFN is now called IFN-α, fibroblast IFN is IFN-β and T cell IFN is IFN-γ. There is also a fourth type of IFN, lymphoblastoid IFN, produced in the "Namalwa" cell line (derived from Burkitt's lymphoma), which seems to produce a mixture of both leukocyte and fibroblast IFN.

The interferon unit or International unit for interferon (U or IU, for international unit) has been reported as a measure of IFN activity defined as the amount necessary to protect 50% of the cells against viral damage. The assay that may be used to measure bioactivity is the cytopathic effect inhibition assay as described (Rubinstein, et al. 1981; Familletti, P. C., et al., 1981). In this antiviral assays for interferon about 1 unit/ml of interferon is the quantity necessary to produce a cytopathic effect of 50%. The units are determined with respect to the international reference standard for Hu-IFN-beta provided by the National Institutes of Health (Pestka, S. 1986).

Every class of IFN contains several distinct types. IFN-β and IFN-γ are each the product of a single gene.

The proteins classified as IFNs-α are the most diverse group, containing about 15 types. There is a cluster of IFN-α genes on chromosome 9, containing at least 23 members, of which 15 are active and transcribed. Mature IFNs-α are not glycosylated.

IFNs-α and IFN-β are all the same length (165 or 166 amino acids) with similar biological activities. IFNs-γ are 146 amino acids in length, and resemble the α and β classes less closely. Only IFNs-γ can activate macrophages or induce the maturation of killer T cells. In effect, these new types of therapeutic agents can be called biologic response modifiers (BRMs), because they have an effect on the response of the organism to the tumor, affecting recognition via immuno-modulation.

In particular, human fibroblast interferon (IFN-β) has antiviral activity and can also stimulate natural killer cells against neoplastic cells. It is a polypeptide of about 20,000 Da induced by viruses and double-stranded RNAs. From the nucleotide sequence of the gene for fibroblast interferon, cloned by recombinant DNA technology, (Derynk et al. 1980) deduced the complete amino acid sequence of the protein. It is 166 amino acid long.

Shepard et al. (1981) described a mutation at base 842 (Cys→Tyr at position 141) that abolished its anti-viral activity, and a variant clone with a deletion of nucleotides 1119-1121.

Mark et al. (1984) inserted an artificial mutation by replacing base 469 (T) with (A) causing an amino acid switch from Cys→Ser at position 17. The resulting IFN-β was reported to be as active as the 'native' IFN-β and stable during long-term storage (−70° C.).

REBIF (recombinant human interferon-β) is a recent development in interferon therapy for multiple sclerosis (MS) and represents a significant advance in treatment. REBIF is interferon(IFN)-beta 1a, produced from mammalian cell lines. It was established that interferon beta-1a given subcutaneously three times per week is efficacious in the treatment of Relapsing-Remitting Multiple Sclerosis (RR-MS). Interferon beta-1a can have a positive effect on the long-term course of MS by reducing number and severity of relapses and reducing the burden of the disease and disease activity as measured by MRI (The Lancet, 1998).

Tumor Necrosis Factor, or TNF, previously called Cachectin, is a pleiotropic cytokine released by activated T cells and macrophages. TNF is a member of the interferon, interleukin and colony stimulating factor cytokine network, which has a key role in signaling with regard to the pathogenesis of many infectious and inflammatory diseases by inducing a number of proinflammatory changes, including production of other cytokine and adhesion molecule (Fiers, 1991).

For convenience, the term TNF collectively shall mean, in the entire context of the present application, both Tumor Necrosis Factor-alpha or Tumor Necrosis Factor-beta from animals or humans, together with naturally occurring alleles thereof (Pennica et al., 1984, Wallach et al., 1986, Beutler, B. and Cerami, A. (1987)). TNF-beta, also called lymphotoxin, has a similar activity but is produced by different cell types (lymphocytes and Natural Killer cells) in response to antigenic or mitogenic stimuli (Gray et al., 1984).

Thus, Tumor Necrosis Factor (TNF-α) and Lymphotoxin (TNF-β) are cytokines which have many effects on cells. Some of their effects are likely to be beneficial to the organism: they may destroy, for example, tumor cells or virus infected cells and augment antibacterial activities of granulocytes. In this way, TNF contributes to the defense of the organism against infectious agents and to recovery from injury. But both TNF-α and TNF-β have also been described to have deleterious effects. There is evidence that overproduction of TNF-α can play a major pathogenic role in several diseases. In some diseases, TNF may cause excessive loss of weight (cachexia) by suppressing activities of adipocytes and by causing anorexia and TNF-α was thus called cachectin. It was also described as a mediator of the damage to tissues in rheumatic diseases and as a major mediator of the damage observed in graft-versus-host reactions.

TNF is expressed as a mature 17 kDa protein that is active as a trimer. This complex exerts its biological activity by aggregating their cell surface receptors, which mediate specific effects in different organs and tissues.

TNF exerts its activity, which is required for the normal development and function of immune system, by binding a family of membrane bound receptor molecules including p55 TNF receptor I, defined in the literature also TNF-RI, and p75 TNF receptor, defined in the literature also TNF-RII (Bazzoni and Beutler, 1996). The dominance of TNF-RI in transducing TNF signal is suggested by the ability of agonistic antibodies specific for this receptor to mimic the majority of TNF induced responses (Shalaby et al., 1990). By binding to its membrane-bound receptors, TNF triggers the signaling pathway through cytoplasmic mediators like TRADD and TRAP-1 (for TNF-RI) or TRAF-1 and TRAF-2 (for TNF-RII), leading to different cell response, like T cell proliferation, tumor-cell lysis in vitro, dermal necrosis, insuline resistance, apoptosis. The extracellular portions of both TNF receptors can be shed and these soluble receptors retain the ability to bind TNF, inactivating TNF activity by formation of high affinity complexes, thereby reducing the binding of TNF to target cell membrane receptors (Nophar et al., 1990).

Based on the finding that TNF-alpha immunoreactivity has been found in high levels in MS lesions, TNF has been described to play a role in the pathogenesis of multiple sclerosis (Darlington, 1999). Therefore, it was generally thought that TNF should be blocked or reduced in order to treat MS, and TNF blocking agents have been suggested for treatment of multiple sclerosis (Selmaj et al., 1995). However, experiments using mice lacking TNF, so-called TNF −/− mice, showed that these mice developed severe neurological impairment with extensive inflammation and demyelination upon induction of a MS like disease with the protein MOG (Liu et al., 1998).

Truncated forms of the TNF-RI (p55) and TNF-RII (p75) receptors mentioned above are described e.g. in EP914431. These soluble receptors are called TBPI and TBPII, respectively (Engelmann et al., 1990). The natural and recombinant soluble TNF receptor molecules, and methods of their production have been described e.g. in the European Patents EP 308 378, EP 398 327 and EP 433 900. EP 398 327 describes that TBPs are not only inhibitors of TNF activity, but also maintain the beneficial effect of TNF. It has also been described that the soluble TNF-receptors stabilize the bioactivity of TNF and thus augment some of its effects (Aderka et al., 1992).

A TNF-like activity was also shown for antibodies directed against the soluble forms of the TNF-receptors (Engelmann et al., 1990).

In addition to this, EP 880 970 discloses the use of TBPs for treatment of multiple sclerosis.

SUMMARY OF THE INVENTION

The present invention is based on the finding that the administration of Tumor Necrosis Factor (TNF) in combination with an interferon (IFN) has a beneficial effect on remyelination and significantly reduces clinical signs of the disease in an in vivo model of multiple sclerosis. It has been surprisingly found that TNF potentiates the therapeutic effect of IFN in multiple sclerosis. It has further been shown that interferon exerts its beneficial effect also at sub-therapeutic dosage, when administered in combination with TNF.

Therefore, it is a first object of the present invention to use an agent having, stimulating or maintaining Tumor Necrosis Factor (TNF) activity, in combination with an interferon (IFN), or an isoform, mutein, fused protein, functional derivative, active fraction or salt thereof, for the manufacture of a medicament for treatment and/or prevention of a demyelinating disease, for simultaneous, sequential or separate use.

It is a second object of the present invention to provide for a pharmaceutical composition containing an agent having, stimulating or maintaining TNF activity in combination with an effective amount of an IFN, in the presence of one or more pharmaceutically acceptable excipients.

BRIEF DESCRIPTION OF THE DRAWINGS

FIG. 2 shows the disease development in the murine EAE model after administration of IFN-beta (subcutaneous daily administration) or TNF-alpha (intravenous administration, every other day) alone or in combination. FIG. 2A shows the mortality rate in this experiment. FIG. 2C shows the results of the histological analysis of the spinal cord, measuring the extent of inflammation (hatched horizontally) expressed as number of perivascular inflammatory infiltrates (PII) or demyelination (hatched vertically), expressed as percent demyelination (% Dem). N.E.=not evaluated.

FIG. 4 shows the disease development in the murine EAE model after administration of IFN-beta (subcutaneous daily administration) or TNF-alpha (intraperitoneal administration, every other day) alone or in combination. FIG. 4A shows the mortality rate in this experiment. FIG. 4C shows the results of the histological analysis of the spinal cord, measuring the extent of inflammation (hatched horizontally) expressed as number of perivascular inflammatory infiltrates (PII) or demyelination (hatched vertically), expressed as percent demyelination (% Dem). N.E.=not evaluated.

DETAILED DESCRIPTION OF THE INVENTION

Figure 1:
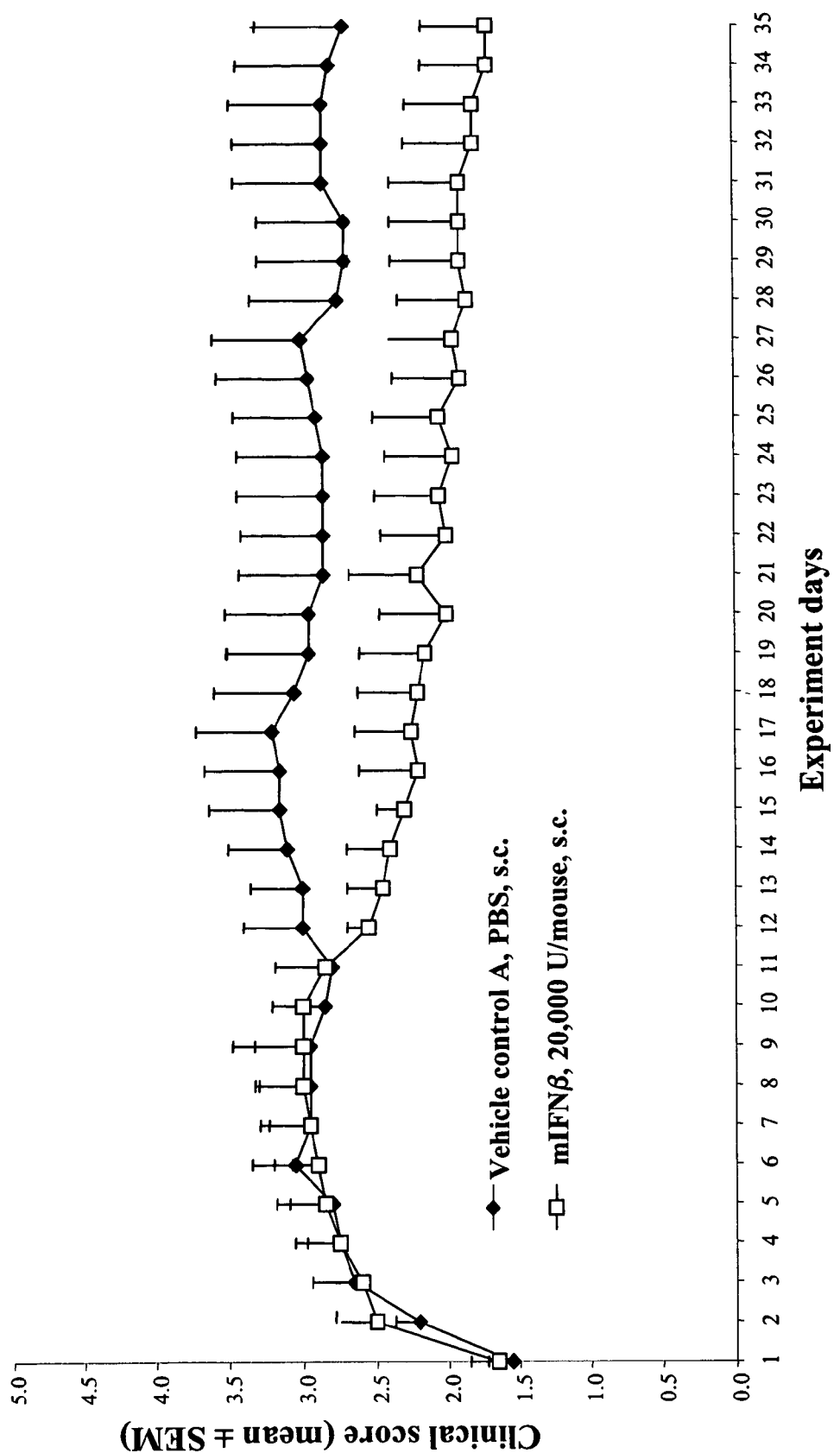
FIG. 1 shows the clinical scores measured daily during an experimental period of 35 days in the murine EAE model after subcutaneous (s.c.) daily administration of either 20000 U/mouse of murine IFN-beta (open squares) or vehicle (filled diamonds).

In accordance with the present invention, it has been surprisingly found that TNF and interferon, when administered in combination, have a pronounced beneficial effect on the clinical severity of multiple sclerosis. It was shown that TNF enhances the therapeutic activity of IFN in an in vivo model of multiple sclerosis.

Therefore, the invention relates to the use of an agent having, stimulating or maintaining Tumor Necrosis Factor (TNF) activity for the manufacture of a medicament for treatment and/or prevention of a demyelinating disease. In accordance with the present invention, the agent having, stimulating or maintaining TNF activity, and the interferon may be used simultaneously, sequentially or separately.

The term "agent having, stimulating or maintaining TNF activity" may be e.g. a protein, peptide or small molecular weight compound having a TNF-like activity, or triggering or stimulating production and/or release of TNF, or enhancing signal transduction via a TNF-receptor. Such agent may also prevent TNF degradation, for example. It may also be an agent enhancing, augmenting or stimulating TNF activity. An agent having, stimulating or maintaining TNF activity may further be any agent stabilizing or preserving the TNF activity. Examples for such agents include antibodies directed against soluble forms of TNF receptors, called TNF binding proteins (TBPs), for instance.

The term "prevention" within the context of this invention refers not only to a complete prevention of the disease or one or more symptoms of the disease, but also to any partial or substantial prevention, attenuation, reduction, decrease or diminishing of the effect before or at early onset of disease.

The term "treatment" within the context of this invention refers to any beneficial effect on progression of disease, including attenuation, reduction, decrease or diminishing of the pathological development after onset of disease.

A "demyelinating disease", as used in the context of the present invention, is a disease involving abnormalities in myelin sheaths of the nervous system, in particular destruction of myelin, as described in detail in the "Background of the Invention" above.

An "interferon" or "IFN", as used herein, is intended to include any molecule defined as such in the literature, comprising for example any types of IFNs mentioned in the above section "Background of the Invention". In particular, IFN-α, IFN-β and IFN-γ are included in the above definition. IFN-β is the preferred IFN according to the present invention. The use of interferons of human origin is also preferred in accordance with the present invention. The term interferon, as used herein, is intended to encompass salts, functional derivatives, variants, analogs and active fragments thereof.

The term "interferon-beta (IFN-β)", as used herein, is intended to include human fibroblast interferon, as obtained by isolation from biological fluids or as obtained by DNA recombinant techniques from prokaryotic or eukaryotic host cells, as well as its salts, functional derivatives, variants, analogs and active fragments.

A "Tumor Necrosis Factor" or "TNF", as used herein, shall mean both Tumor Necrosis Factor-alpha and/or Tumor Necrosis Factor-beta from animals or humans, together with naturally occurring alleles thereof (Pennica et al., 1984), as well as its salts, functional derivatives, variants, analogs and active fragments. The use of human TNF is preferred in accordance with the present invention.

In a preferred embodiment, the agent having, stimulating or maintaining Tumor Necrosis Factor (TNF) activity is a TNF, or an isoform, mutein, fused protein, functional derivative, active fraction or salt thereof.

Tumor Necrosis Factor Binding Protein (TBP) has been shown to maintain the prolonged beneficial effect of TNF. Therefore, in an alternative preferred embodiment, the agent having, stimulating or maintaining Tumor Necrosis Factor (TNF) activity is a TBP, or an isoform, mutein, fused protein, functional derivative, active fraction or salt thereof, in combination with an interferon (IFN), or an isoform, mutein, fused protein, functional derivative, active fraction or salt thereof.

The term "TBP", or "TBPs", as used herein, relates to both TNF binding protein I, comprising an extracellular portion of the p55 TNF receptor, and TNF binding protein II, comprising an extracellular portion of the p75 TNF receptor, or a mixture of both. In accordance with the present invention, interferon may be used in combination with either TBPI or TBP II alone, or both. The components may be used simultaneously, sequentially or separately.

In accordance with the present invention, the TBP to be administered in combination with IFN may be TBP I. In a preferred embodiment, it is TBP II.

A "TNF binding protein" or "TBP" may be a soluble fragment comprising all or a portion of the extracellular domain of either of the two known TNF receptors. Preferably, it TBP I or TBP II, as described above in the background of the invention.

In accordance with the present invention, an agent having, stimulating or maintaining TNF activity may also be a molecule stimulating one or both of the TNF receptors. Examples of such molecules could be e.g. lipopolysaccharides, glucanes, or IL-1.

In the following, the agent having, stimulating or maintaining TNF activity, and in particular TNF and IFN and TBP, may also be referred to as "substance(s) of the invention".

As used herein the term "muteins" refers to analogs of a substance according to the invention, in which one or more of the amino acid residues of a natural substance of the invention are replaced by different amino acid residues, or are deleted, or one or more amino acid residues are added to the natural sequence of substance of the invention, without changing considerably the activity of the resulting products as compared to the wild type substance of the invention. These muteins are prepared by known synthesis and/or by site-directed mutagenesis techniques, or any other known technique suitable therefor.

Any such mutein preferably has a sequence of amino acids sufficiently duplicative of that of a substance of the invention, such as to have substantially similar or even better activity to a substance of the invention. The biological function of interferon and TNF are well known to the person skilled in the art, and biological standards are established and available e.g. from the National Institute for Biological Standards and Control (See Worldwide Website: immunology.org/links/NIBSC).

Bioassays for the determination of IFN or TNF or TBP activity have been described. An IFN assay may for example be carried out as described by Rubinstein et al., 1981. The cytotoxic activity of TNF can be measured according to Flick and Gifford, 1984, for instance. The effect of a TBP may e.g. be tested as described in EP 308 378 or EP 398 327. Thus, it can be determined whether any given mutein has substantially a similar, or even a better, activity than TNF or IFN by means of routine experimentation.

Muteins of a substance of the invention, which can be used in accordance with the present invention, or nucleic acid coding therefor, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of polypeptides or proteins of the invention, may include synonymous amino acids within a group which have sufficiently similar physicochemical properties that substitution between members of the group will preserve the biological function of the molecule. It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins a substance of the invention, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al). Specific muteins of TNF-alpha have been described in U.S. Pat. No. 5,891,679, for instance. Specific muteins of IFN-beta have been described, for example by Mark et al., 1984.

The term "fused protein" refers to a polypeptide comprising a substance of the invention, or a mutein thereof, fused to another protein, which e.g., has an extended residence time in body fluids. A substance of the invention may thus be fused to another protein, polypeptide or the like, e.g., an immunoglobulin or a fragment thereof.

"Functional derivatives" as used herein cover derivatives of a substance of the invention, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity a substance of the invention, and do not confer toxic properties on compositions containing it. These derivatives may, for example, include polyethylene glycol side-chains, which may mask antigenic sites and extend the residence of a substance of the invention in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "active fractions" of a substance of the invention, or muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has no significantly reduced activity as compared to the corresponding substance of the invention.

The term "salts" herein refers to both salts of carboxyl groups and to acid addition salts of amino groups of the proteins described above or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of the proteins (IFN and TNF, respectively) relevant to the present invention, i.e., the ability to bind to the corresponding receptor and initiate receptor signaling.

Demyelinating diseases according to the invention may be e.g. multiple sclerosis, acute disseminated encephalomyelitis, acute inflammatory peripheral neuropathies adrenoleukodystrophy and adrenomyeloneuropathy, Leber's hereditary optic atrophy, or HTLV-associated myelopathy, as described in the introduction. They may preferably be neuropathies with abnormal myelination. They may concern the peripheral or the central nervous system.

The most common demyelinating disease is multiple sclerosis. Therefore, in a preferred embodiment of the invention, the combination of a TNF or TBP and an interferon is used for treatment and/or prevention of multiple sclerosis (MS). In accordance with the present invention, MS may have a chronic progressive disease development. It may also be relapsing-remitting multiple sclerosis.

In accordance with the present invention, the use of recombinant human IFN-beta and recombinant human TNF-alpha are especially preferred.

In an alternative embodiment, the use of recombinant human IFN-beta and recombinant TBP I or II is preferred.

A special kind of interferon variant has been described recently. The so-called "consensus interferons" are non-naturally occurring variants of IFN (U.S. Pat. No. 6,013,253). Consensus interferons were shown to be effective in the treatment of multiple sclerosis.

Therefore, in a preferred embodiment of the invention, TNF is used in combination with a consensus interferon.

As used herein, human interferon consensus (IFN-con) shall mean a non-naturally-occurring polypeptide, which predominantly includes those amino acid residues that are common to a subset of IFN-alpha's representative of the majority of the naturally-occurring human leukocyte interferon subtype sequences and which includes, at one or more of those positions where there is no amino acid common to all subtypes, an amino acid which predominantly occurs at that position and in no event includes any amino acid residue which is not existant in that position in at least one naturally-occurring subtype. IFN-con encompasses but is not limited to the amino acid sequences designated IFN-con1, IFN-con2 and IFN-con3 which are disclosed in U.S. Pat. Nos. 4,695,623, 4,897,471 and 5,541,293. DNA sequences encoding IFN-con may be produced as described in the above-mentioned patents, or by other standard methods.

In a further preferred embodiment, the fused protein comprises an Ig fusion. The fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met (SEQ ID NO:1) introduced between the sequence of the substances of the invention and the immunoglobulin sequence. The resulting fusion protein has improved properties, such as an extended residence time in body fluids (half-life), increased specific activity, increased expression level, or the purification of the fusion protein is facilitated.

In a preferred embodiment, IFN and/or TNF is fused to the constant region of an Ig molecule. Preferably, it is fused to heavy chain regions, like the CH2 and CH3 domains of human IgG1, for example. Other isoforms of Ig molecules are also suitable for the generation of fusion proteins according to the present invention, such as isoforms $IgG_2$ or $IgG_4$, or other Ig classes, like IgM or IgA, for example. Fusion proteins may be monomeric or multimeric, hetero- or homomultimeric.

The present invention relates to the combined treatment of a TNF and/or TBP and an IFN. The therapeutic entities could also be liked to each other in order to be able to administer one single molecule, be it monomeric or multimeric, instead of two or three separate molecules. A multimeric fusion protein could comprise a TNF fused to an Ig moiety, as well as an IFN fused to an Ig moiety. If expressed together, the resulting fusion protein, which may be linked by disulfide bridges, for instance, will comprise both TNF and IFN or TBP and IFN, respectively. The compounds of the present invention may further be linked by any other cross-linking agent or moiety, such as a polyethylene molecule, for instance.

In a further preferred embodiment, the functional derivative comprises at least one moiety attached to one or more functional groups, which occur as one or more side chains on the amino acid residues. Preferably, the moiety is a polyethylene (PEG) moiety. PEGylation may be carried out by known methods, such as the ones described in WO99/55377, for example.

Standard dosages of human IFN-beta presently used in the treatment of relapsing-remitting MS are ranging from 80 000 IU/kg and 200 000 IU/kg per day or 6 MIU (million international units) and 12 MIU per person per day or 22 to 44 mg per person. In accordance with the present invention, it has been surprisingly shown that TNF enhances the therapeutic effect of IFN in an established model of multiple sclerosis. Therefore, in accordance with the present invention, IFN may be administered at a dosage of about 1 to 50 mg, preferably of about 10 to 30 mg, more preferably of about 10 to 20 mg per person per day, together with TNF. The preferred route of administration is subcutaneous administration, administered three times a week. A further preferred route of administration is the intramuscular administration, which may be applied once a week.

TNF-alpha therapy has been used in cancer treatment so far. From studies in cancer patients, it is known that toxicity of r-TNF-alpha treatment is variable and not always dose-dependent. Hepatic and cardiovascular toxicity have been generally found to increase with increasing dose, but constitutional symptoms like fever, chills, or rigors seem not to be dose-related. The maximum tolerated dose of r-TNF-alpha, administered intravenously over 30 min, is reported to be between 100 and 300 $\mu g/m^2$ (Feinberg et a., 1988 ; Gamm et al., 1991; Schiller et al., 1991).

Therefore, in a further preferred embodiment, TNF-alpha is administered in a sub-toxic concentration. More preferably, the sub-toxic concentration is less than 100 $\mu g/m^2$, preferably less than 50 $\mu g/m^2$, more preferably less than 10 $\mu g/m^2$, and most preferably less than 1 $\mu g/m^2$.

In accordance with the present invention, TBP is used in a dosage of about 1 to 300 mg per person per day. Preferably, TBP may be used in a dosage of about 150 mg per person per day or about 100 mg per person per day or about 50 mg per person per day or about 35 mg per person per day or about 25 mg per person per day or about 10 mg per person per.

TBP may be administered daily or every other day. It may e.g. be administered daily at 10 mg per person per day. It may further be administered twice or three tmes per week. In this case it may e.g. be administered at 25, 35 or 50 mg per person per day.

The administration of such active ingredients may be by intravenous, intramuscular or subcutaneous route. The preferred route of administration for IFN and/or TNF is the subcutaneous route. For TNF, a further preferred route is the intravenous administration.

Corticosteroids are theraprutically efficacious in the treatment of demyelinating diseases. Therefore, the medicament of the invention may further comprise a corticosteroid, for simultaneous, sequential, or separate use. As corticosteroid treatment, oral prednisone 60 to 100 mg/day tapered over 2 to 3 weeks or IV methylprednisolone 500 to 1000 mg/day for 3 to 5 days may be administered, for instance.

Glatiramer is a synthetic co-polymer with similarities to myelin basic protein and is administered by daily subcutaneous injection. It has also been proved to have a therapeutic effect in multiple sclerosis. In a preferred embodiment of the invention, the medicament further comprises glatiramer, for sequential, separate or simultaneous use.

The invention further relates to a pharmaceutical composition comprising an agent having, stimulating or maintaining TNF activity, in combination an IFN, in the presence of one or more pharmaceutically acceptable excipients. Preferably, the pharmaceutical composition of the invention may comprise a TNF or a TBP, in combination with an Interferon.

The pharmaceutical composition of the invention may further comprise a corticosteroid and/or glatiramer.

The term "pharmaceutically acceptable" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

The active ingredients of the pharmaceutical composition according to the invention can be administered to an individual in a variety of ways. The routes of administration include intradermal, transdermal (e.g. in slow release formulations), intramuscular, intraperitoneal, intravenous, subcutaneous, oral, epidural, topical, and intranasal routes. Any other therapeutically efficacious route of administration can be used, for example absorption through epithelial or endothelial tissues or by gene therapy wherein a DNA molecule encoding the active agent is administered to the patient (e.g. via a vector), which causes the active agent to be expressed and secreted in vivo. In addition, the protein(s) according to the invention can be administered together with other components of biologically active agents such as pharmaceutically acceptable surfactants, excipients, carriers, diluents and vehicles.

The subcutaneous route is preferred in accordance with the present invention.

Another possibility of carrying out the present invention is to activate endogenously the genes for the compounds of the invention, i.e. TNF and/or IFN. In this case, a vector for inducing and/or enhancing the endogenous production of TNF and/or IFN in a cell normally silent for expression of TNF and/or IFN, or which expresses amounts of TNF and/or IFN which are not sufficient, are is used for treatment of a demyelinating disease. The vector may comprise regulatory sequences functional in the cells desired to express TNF and/or IFN. Such regulatory sequences may be promoters or enhancers, for example. The regulatory sequence may then be introduced into the right locus of the genome by homologous recombination, thus operably linking the regulatory sequence with the gene, the expression of which is required to be induced or enhanced. The technology is usually referred to as "endogenous gene activation" (E.G.A), and it is described e.g. in WO 91/09955.

The invention further relates to the use of a cell that has been genetically modified to produce IFN and/or TNF in the manufacture of a medicament for the treatment and/or prevention of neurological diseases.

For parenteral (e.g. intravenous, subcutaneous, intramuscular) administration, the active protein(s) can be formulated as a solution, suspension, emulsion or lyophilised powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The bioavailability of the active protein(s) according to the invention can also be ameliorated by using conjugation procedures which increase the half-life of the molecule in the human body, for example linking the molecule to polyethylenglycol, as described in the PCT Patent Application WO 92/13095.

The dosage administered, as single or multiple doses, to an individual will vary depending upon a variety of factors, including pharmacokinetic properties, the route of administration, patient conditions and characteristics (sex, age, body weight, health, size), extent of symptoms, concurrent treatments, frequency of treatment and the effect desired.

The substances of the invention may be administered daily or every other day, of less frequent. Preferably, one or more of the substances of the invention are administered one, twice or three times per week.

The daily doses are usually given in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease.

According to the invention, the substances of the invention can be administered prophylactically or therapeutically to an individual prior to, simultaneously or sequentially with other therapeutic regimens or agents (e.g. multiple drug regimens), in a therapeutically effective amount. Active agents that are administered simultaneously with other therapeutic agents can be administered in the same or different compositions.

The invention further relates to a method of treatment and/or prevention of a demyelinating disease comprising administering to a host in need thereof a therapeutically effective amount of an agent having, stimulating or maintaining TNF activity, and a therapeutically effective amount of an interferon.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

Having now described the invention, it will be more readily understood by reference to the following examples that are provided by way of illustration and are not intended to be limiting of the present invention.

EXAMPLE

Effect of TNF-alpha Alone, or in Combination with IFN-beta, in an in vivo Model of Multiple Sclerosis The effect of TNF-alpha, either alone or in combination with IFN-beta, on disease development was assayed using an established animal model of multiple sclerosis (MS). The experimental autoimmune encephalomyelitis (EAE) model is a murine chronic demyelinating model.

EAE Induction Protocol

Experimental autoimmune encephalomyelitis (EAE) was induced in groups of mice as follows: groups of C57black6/J female mice were immunized subcutaneously into the right flank at day 0 with 200 µl emulsion, containing 200 µg of a synthetic peptide corresponding to Myelin Oligodendrocyte Glycoprotein (MOG 35-55 (Neosystem, Strasbourg, France) in Complete Freund's Adjuvant containing 5 mg/ml of H37RA *Mycobaterium tuberculosis*.

Immediately, and at day 2, the animals received an intraperitoneal injection of 500 ng pertussis toxin dissolved in 400 µl of pertussis buffer (0.5 M NaCl, 0.015 M Tris pH 7.5, 0.017% Triton X-100). At day 7, the animals received a boost of identical amount (200 µl) of emulsion, containing 200 µg MOG35-55 peptide in Complete Freund's Adjuvant, into the left flank.

Treatment with all the drugs was started individually in each animal when reaching a clinical score $\geq 1$. These animals were treated daily with 200 µl of either:
1) phosphate buffered saline (PBS), administered s.c. (subcutaneous) and i.v. (intravenous);
2) murine mIFN-beta at 20,000 U/mouse, administered s.c.;
3) murine mIFN-beta at 5,000 U/mouse, administered s.c.;
4) r-mTNFa at 0.1 µg/mouse, administered i.v. or i.p.
5) combined r-mTNF-alpha (0.1 µg/mouse, i.v. or i.p., respectively) and mIFNbeta (5,000 U/mouse, s.c.).

Two routes of administration were chosen for TNF-alpha: The i.v. route in was chosen on the basis of results published by Liu et al. (Nature Medicine 1998 4: 78-83). The i.p. route was chosen to overcome the toxicity problems met during studies with higher doses of TNF-alpha.

PBS was used as vehicle and all substances were injected subcutaneously in the neck, whereby the group treated with two substances was injected twice into two different sites. Animals were scored daily for neurological signs according to the scale indicated below. Weight loss and clinical score of individual animals were monitored daily up to day 35 after disease onset, using international standard of scoring by following criteria:
0=no signs of disease
1=tail weakness or paralysis
2=tail paralysis+hindlimb(s) weakness or partial paralysis
3=tail paralysis+complete hindlimb paralysis
3.5=tail paralysis+hindlimb paralysis+incontinence
4=tail paralysis+hindlimbs paralysis+weakness or paralysis of forelimbs
5=moribund.

Differences among experimental groups in the time-course of clinical score were analyzed by Kruskal-Wallis test followed, in case of significance, by the pairwise Wilcoxon test, at each measurement time.

Histological Analysis

At the end of the treatment period, each animal was anesthetised with an i.p. injection of sodium pentobarbital (about 50 mg/kg) and, after blood sampling, transcardially perfused-fixed with 4% paraformaldehyde via the left ventricle. Fixed spinal cords were carefully dissected out. Spinal cord slices (10 to 12 slices per animal) were embedded in paraffin blocks, sectioned and stained with hematoxylin and eosin for evaluation of inflammatory signs and with Kluver-PAS staining (Luxol Fast Blue plus Periodic Acid Schiff stainings) for detection of demyelination. In the spinal cord, the total area of all slices was measured for each animal as points of intersection of a 10×10 grid at a magnification of 0.4×0.4 mm per grid. The perivascular inflammatory infiltrates (PII) were counted in each slice in order to obtain a total value for each animal and evaluated as number of infiltrates per $mm^2$. Demyelination are as were measured for each animal as points of intersection of 10×10 grid at a magnification of 0.1×0.1 mm per grid and were expressed as a percentage of total demyelination (Dem) area over the total area of the slices. Differences among experimental groups were assessed by one-way ANOVA followed by Newman-Keuls test.

Results

In experiments aimed at finding the final study protocol, the first animals became sick when treated with r-mTNF-alpha at doses of 1 and 10 μg/mouse i.v. every second day. Since after one or two administrations, all treated animals died, it was decided to reduce the doses to 0.1 μg/mouse and to administer the compound by i.p and i.v. routes in two experimental groups, respectively.

The following study protocol was applied:

| Test Substance | Dose | Administration route | Frequency | Treatment period (Days) |
|---|---|---|---|---|
| r-mTNFα | 0.1 μg/mouse | i.p. | Every second day | 35 |
| r-mTNFα | 0.1 μg/mouse | i.v. | Every second day | 35 |
| r-mTNFα + mIFNβ | 0.1 μg/mouse + 5,000 U/mouse | i.p. + s.c. | Every second day + Daily | 35 |
| r-mTNFα + mIFNβ | 0.1 μg/mouse + 5,000 U/mouse | i.v. + s.c. | Every second day + Daily | 35 |

FIG. 1 depicts the result of a positive control experiment, wherein 20,000 IU interferon-beta/mouse were administered subcutaneously every day. As compared to the administration of vehicle only, and as expected, IFN-beta showed a beneficial effect on the development of the disease from day 12 on, as shown by a marked reduction in clinical score (open squares).

Figure 2B:
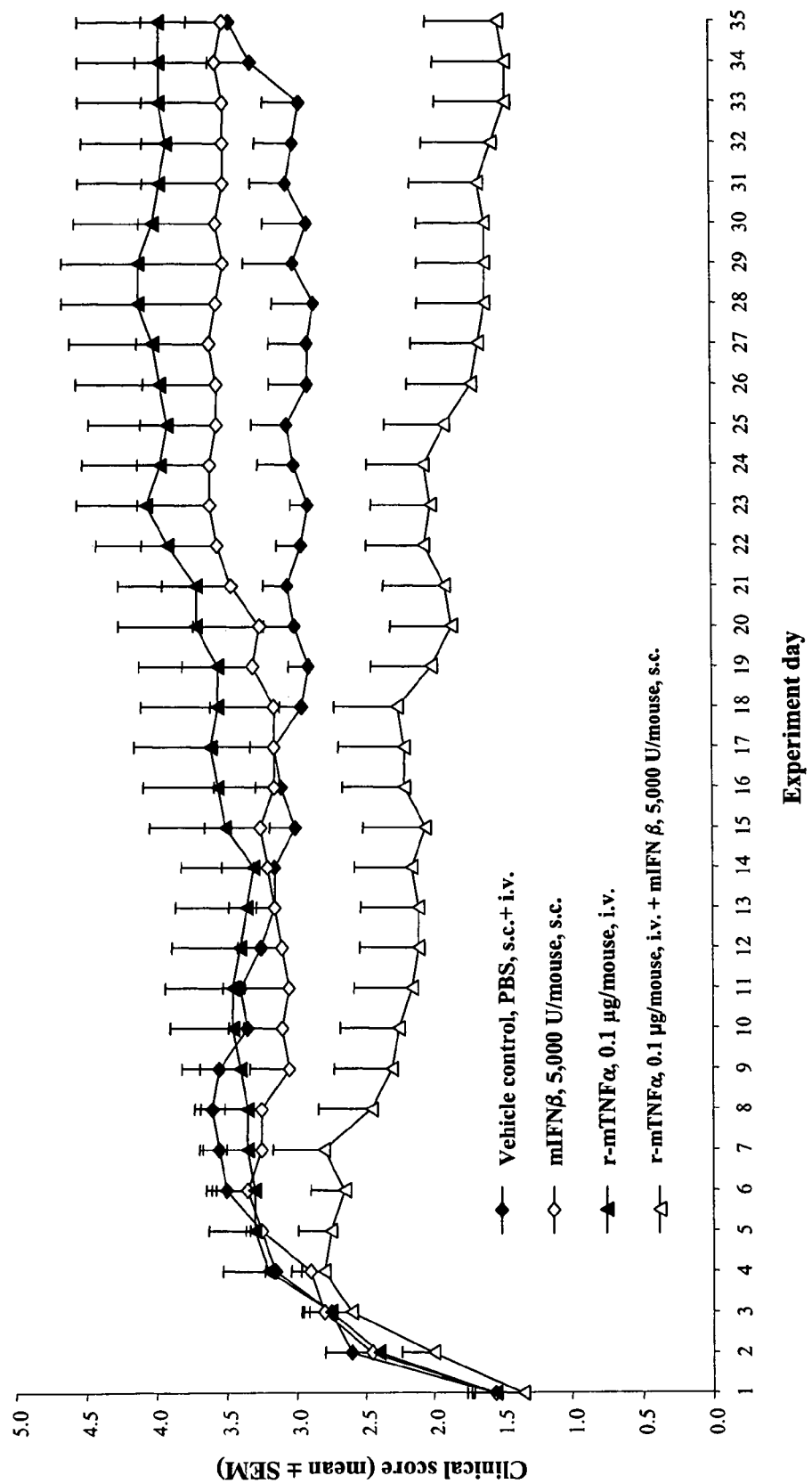
FIG. 2B shows the clinical scores during an experimental period of 35 days after subcutaneous (s.c.) and intravenous (i.v.) administration of vehicle (filled diamonds), s.c. administration of 5,000 U/mouse of murine IFN-beta (open diamonds), intravenous (i.v.) administration of 0.1 μg/mouse of murine TNF-alpha (filled triangles) or administration of both 0.1 μg/mouse mTNF-alpha i.v. and 5,000 U/mouse mIFN-beta s.c. (open triangles). A clinical score of 5 was assigned to dead animals from the day of death until the end of the experiment (FIG. 2B).
Figure 3A:
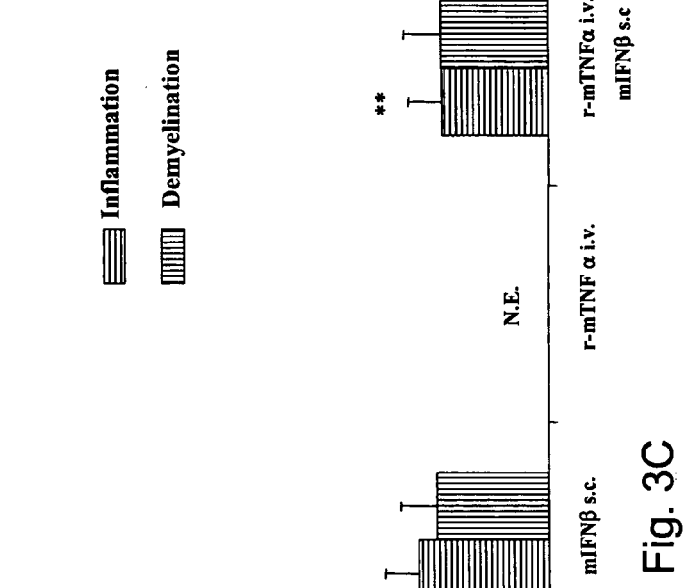
FIG. 3 shows the data of FIG. 2, evaluated in a different way. Those animals dying during the experimental period were not scored, but dropped out completely.
Figure 3C:
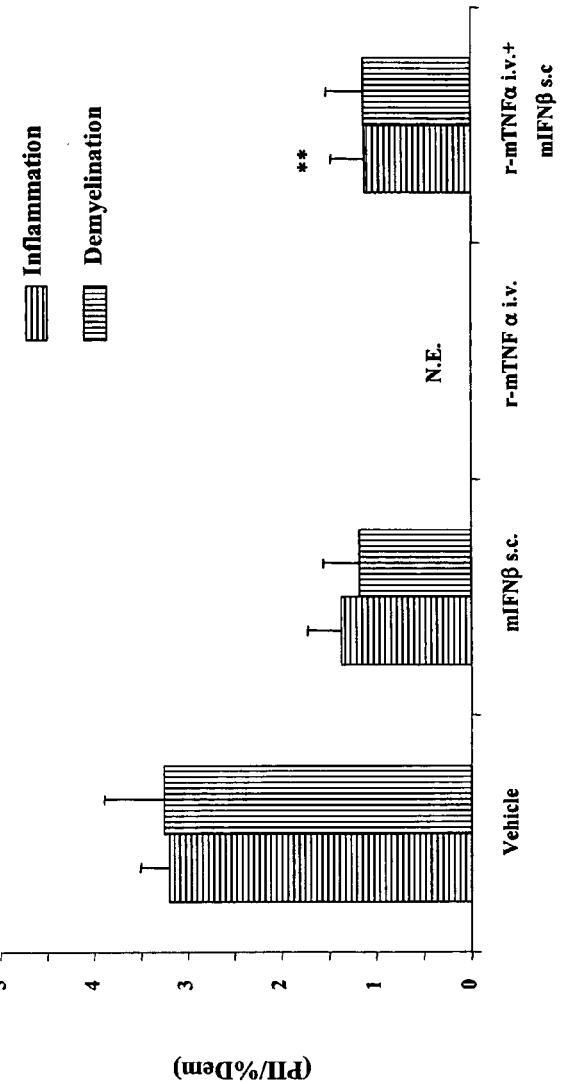
Figure 3B:
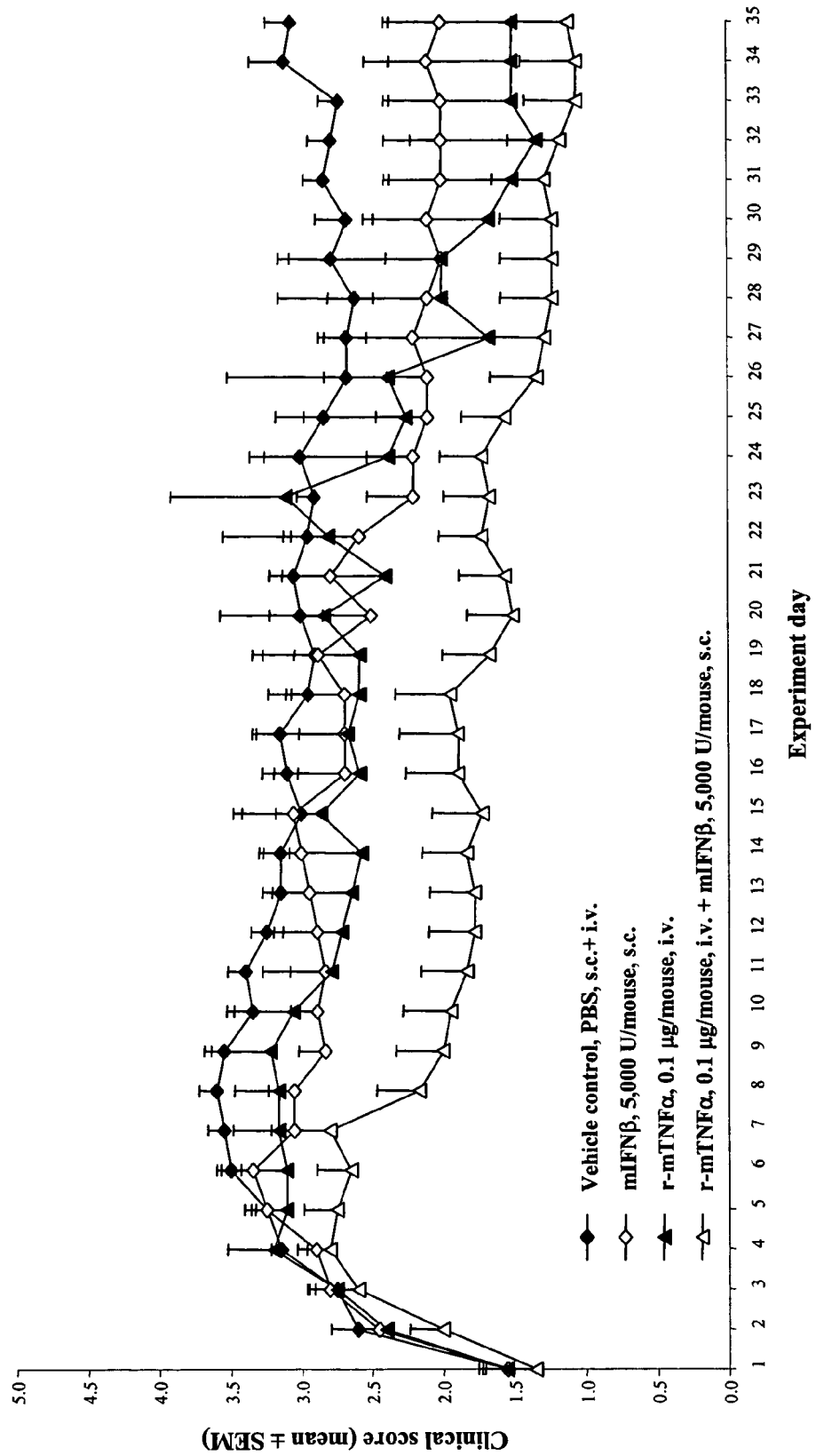

The effects of an intravenous administration of a four times lower amount of IFN-beta, i.e. of 5,000 IU/mouse, are shown in FIGS. 2 and 3. Two ways of evaluating the results were used: either a clinical score of 5 was assigned to dead animals from the day of death until the end of experiment, the outcome of this way of data evaluation are depicted in FIG. 2. In the second way of data evaluation the animals were scored until their death and then dropped out completely. The results are shown in FIG. 3.

FIGS. 2/3A show the mortality rate in this series of experiments. As expected in this animal model, the mortality rate was variable. However, a strikingly low mortality rate was achieved in those animals receiving administration of both TNF-alpha and IFN-beta.

FIGS. 2/3B shows the development of clinical score over the experimental period of 35 days. The administration of 5,000 IU/mouse s.c. every day did not result in any amelioration of the clinical score (open diamonds). An administration of 0.1 μg/mouse of TNF-alpha intravenously (FIG. 2B, filled triangles) resulted in a slight improvement of clinical score as compared to vehicle, in particular at later stages of the disease (FIG. 3 B). However, this improvement was not statistically significant, especially given the high mortality rate of mice which received TNF-alpha alone.

Combined administration of TNF-alpha (i.v.) and IFN-beta (s.c.) resulted in a significant improvement (at interval days 6-14 and 19-35, FIG. 2B, and from day 6 through day 35, FIG. 3B) of clinical scores during the test period of 35 days (open triangles).

The histological analysis is depicted in FIGS. 2/3C. The histology of the spinal cord showed that treatment with IFN-beta alone, and the combination of TNF-alpha and IFN-beta in combination, resulted in a reduced extent of inflammation ($p<0.01$ versus the vehicle-treated group, only for the combined treatment) and demyelination.

Figure 4B:
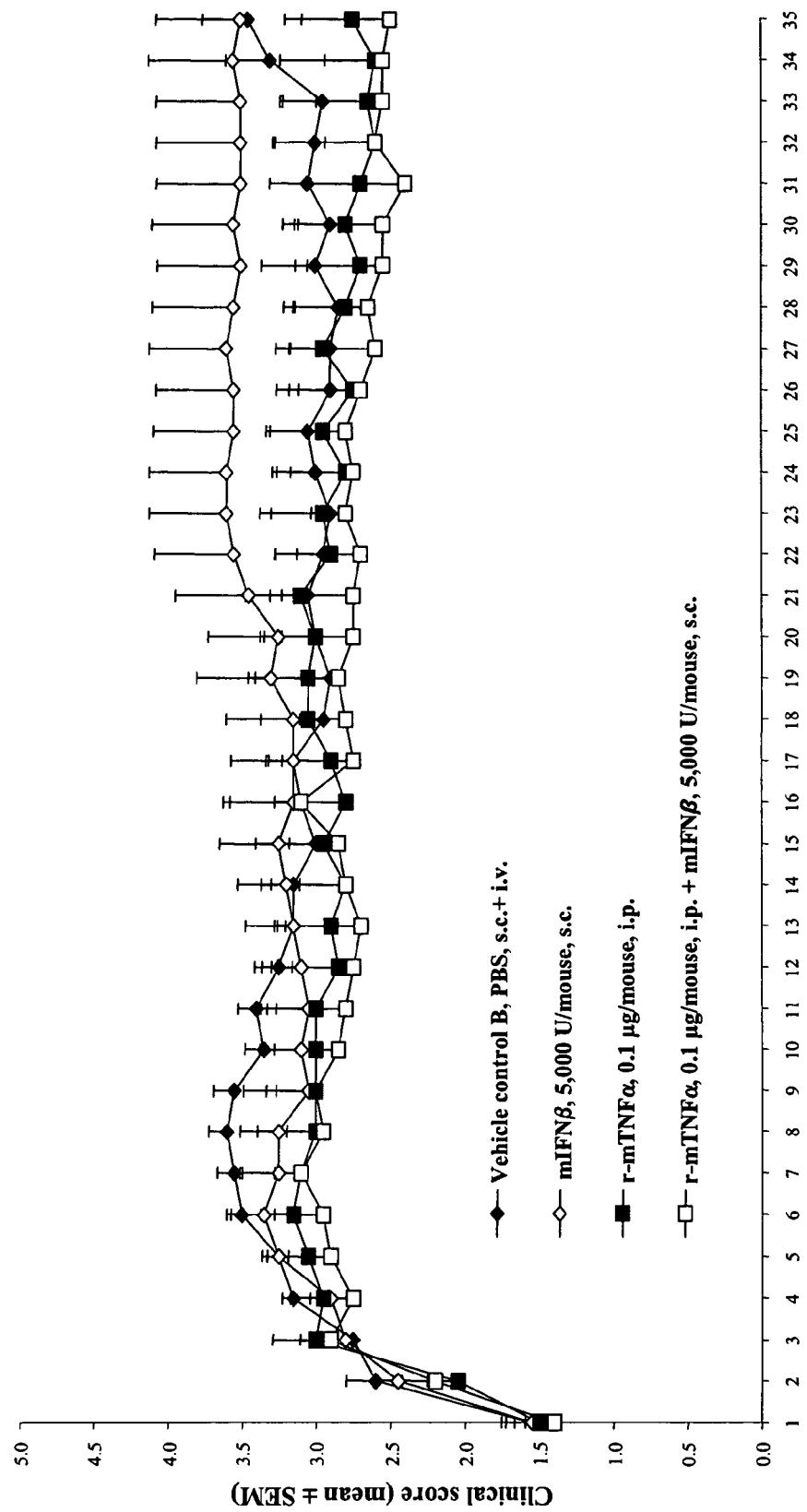
FIG. 4B shows the clinical scores during an experimental period of 35 days after subcutaneous (s.c.) and intraperitoneal (i.p.) administration of vehicle (filled diamonds), s.c. administration of 5,000 U/mouse of murine IFN-beta (open diamonds), i.p. administration of 0.1 μg/mouse of murine TNF-alpha (filled squares) or administration of both 0.1 μg/mouse mTNF-alpha ip.. and 5,000 U/mouse mIFN-beta s.c. (open squares). A clinical score of 5 was assigned to dead animals from the day of death until the end of the experiment (FIG. 4B).
Figures 5A, 5C:
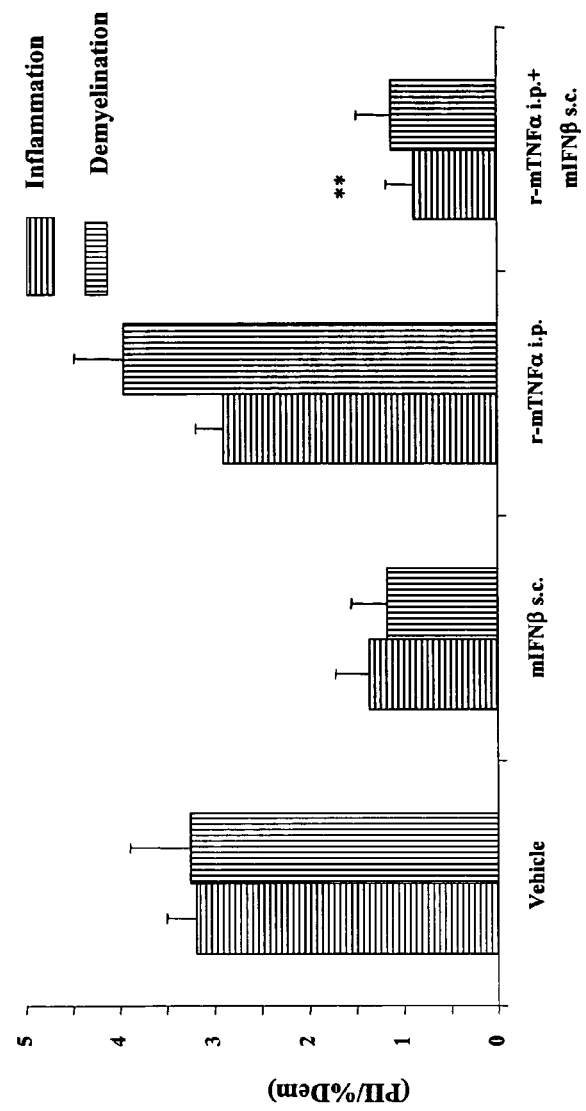
FIG. 5 shows the data of FIG. 4, evaluated in a different way. Those animals dying during the experimental period were not scored, but dropped out completely.
Figure 5B:
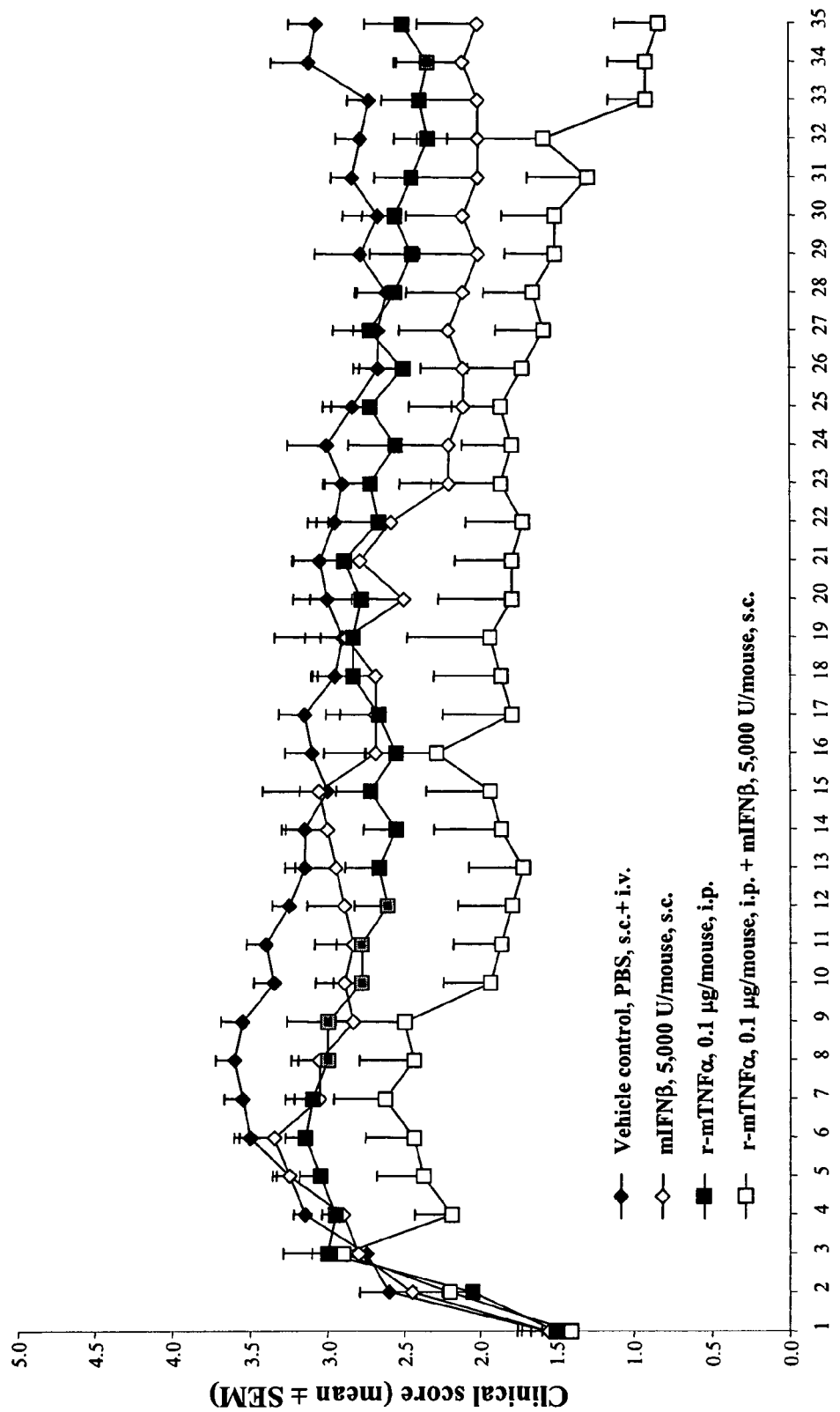

FIGS. 4/5 depict the experiment in which 5,000 U/mouse of IFN-beta s.c. and 0.1 μg/mouse of TNF-alpha i.p. were administered either alone, or in combination. FIG. 4 illustrates the data analysis counting dead animals as clinical score 5, FIG. 5 shows the analysis of the same experiment, except that dead animals were not scored at all anymore.

Administration of IFN-beta in combination with TNF-alpha (open squares) resulted in a slight improvement of the clinical score (with significant improvements in the interval days 8-9, FIG. 4B, and, days 4-15, 16 and 21-35, FIG. 5 B), i.e. the disease development, as compared to the administration of vehicle only. The beneficial effect of the combined treatment could also be observed in the histological analysis of the spinal cords (FIGS. 4/5C), showing in particular a significantly reduced extent of inflammation ($p<0.01$). Taken together, TNF-alpha seems to have a lower effect when administered intraperitoneally as compared to the intravenous route.

Conclusions:

Administration of sub-therapeutic amounts of IFN-beta, in combination with sub-toxic amounts of TNF-alpha, produced a remarkable and long-lasting improvement of the disease, as expressed by reduced clinical scores as well as reduced inflammation and demyelination in the spinal cords of the animals. Therefore, the results presented above show a clear beneficial effect of treatment with a combination of TNF-alpha and IFN-beta, reducing clinical signs of chronic EAE in mice after immunization with MOG. Therefore, TNF enhances the therapeutic effect of interferon in multiple sclerosis. Thus, a combined treatment with TNF and IFN is suggested for treatment of demyelinating diseases such as multiple sclerosis.

REFERENCES

1. Aderka et al., J. Expt. Med. 1992, 175(2), 323-9.
2. Anonymous, The Lancet 352, 1498-1504, (1998);
3. Bazzoni, F. and Beutler, B., 1996, N.Engl.J.Med. 334, 1717-1725.
4. Beutler, B. and Cerami, A. (1987) New England J. Med. 316: 379-385.
5. Clegg and Bryant, Exp. Opin. Parmacother. 2001, 2(4): 623-639;
6. Darlington, Curr. Opin. In CPNS Investigational Drugs 1999 1(5), 578-586
7. Derynk R. et al., Nature 285, 542-547,1980;
8. Engelmann et al., J. Biol. Chem. 1990, 265(24), 14497-504.
9. Familletti,P. C., Rubinstein,S., and Pestka, S. (1981 "A Convenient and Rapid Cytopathic Effect Inhibition Assay for Interferon," in Methods in Enzymology, Vol. 78 (S.Pestka, ed.), Academic Press, New York, 387-394;
10. Feinberg B, Kurzrock R, Talpaz M, Blick M, Saks S, Gutterman J U. A phase I trial of intravenously-administered recombinant tumor necrosis factor-alpha in cancer patients. J Clin Oncol 1988; 6: 1328-1334;
11. Fiers, FEBS Lett. 1991 Jul. 22;285(2):199-212. Review;
12. Flick, D. A., Gifford, G. E.: Comparison of in Vitro Cell Cytotoxic Assays for Tumor Necrosis Factor. J. Immunol. Meth. 68, 1667, 1984;
13. Gamm H, Lindemann A, Mertelsmann R, Herrmann F. Phase I trial of recombinant human tumour necrosis factor a in patients with advanced malignancy. Eur J Cancer 1991; 27: 856-863;
14. Gray P W, Aggarwal B B, Benton C V, Bringman T S, Henzel W J, Jarrett J A, Leung D W, Moffat B, Ng P, Svedersky L P, et al.Nature. 1984 Dec 20-1985 Jan. 2;312(5996):721 4;
15. Liu J, Marino M W, Wong G, Grail D, Dunn A, Bettadapura J, Slavin A J, Old L, Bernard C C. Nat Med 1998 January;4(1):78-83
16. Mark D. F. et al., Proc. Natl. Acad. Sci. U.S.A., 81 (18) 5662-5666 (1984);
17. Nophar, Y., Kemper, O., Brakebusch, C., Englemann, H., Zwang, R., Aderka, D., Holtmann, H., and Wallach, D., 1990, EMBO J. 9, 3269-3278
18. Pestka, S. (1986) "Interferon Standards and General Abbreviations,in Methods in Enzymology (S. Pestka, ed.), Academic Press, New York 119, 14-23;
19. Pennica D, Nedwin G E, Hayflick J S, Seeburg P H, Derynck R, Palladino M A, Kohr W J, Aggarwal B B, Goeddel D V. Nature. 1984 Dec. 20-1985 Jan. 2;312(5996):724-9;
20. Rubinstein, S., Familletti, P. C., and Pestka, S. (1981) "Convenient Assay for Interferons," J. Virol. 37, 755-758;
21. Schiller J H, Storer B E, Witt P L, Alberti D, Tombes M B, Arzoomanian R, Proctor R A, McCarthy D, Brown R, Voss S D, Remick S C, Grem J L, Borden E C, Trump D L. Biological and clinical effects of intravenous tumor necrosis factor-a administered three times weekly. Cancer Res 1991; 51: 1651-1658;
22. Selmaj et al., J. Neuroimmunology 56 (1995) 135-141
23. Shalaby, M. R., Sundan, A., Loetscher, H., Brockhaus, M., Lesslauer, W., and Espevik, T., 1990, J. Exp. Med. 172,1517-1520;
24. Shepard H. M. et al., Nature, 294, 563-565, (1981).
25. Wallach, D. (1986) in: Interferon 7 (ion Gresser, Ed.), pp. 83-122, Academic Press, London.

---

---

The invention claimed is:

1. A method of treating multiple sclerosis comprising the administration of a composition comprising TNF-alpha in combination with IFN-beta or consensus IFN and one or more pharmaceutically acceptable excipients to an individual having multiple sclerosis.

2. The method according to claim 1, wherein said composition comprises TNF-alpha in combination with IFN-beta.

3. The method according to claim 1, wherein said composition comprises TNF-alpha in combination with consensus IFN.

4. The method according to claim 1, wherein said IFN-beta is recombinant human interferon-beta.

5. The method according to claim 1, wherein said consensus IFN is recombinant consensus interferon.

6. The method according to claim 1, wherein said TNF-alpha is recombinant human TNF-alpha.

7. The method according to claim 6, wherein said recombinant human TNF-alpha comprises a TNF-alpha fusion protein.

8. The method according to claim 4, wherein said recombinant interferon beta comprises an interferon-beta fusion protein.

9. The method according to claim 1, wherein said composition further comprises a corticosteroid.

10. The method according to claim 1, wherein said composition further comprises glatiramer.

11. The method according to claim 7, wherein said TNF-alpha fusion protein is an Ig-TNF-alpha fusion protein.

12. The method according to claim 8, wherein said interferon-beta fusion protein is an Ig-interferon beta fusion protein.

13. The method according to claim 5, wherein said recombinant consensus interferon comprises a recombinant consensus interferon fusion protein.

14. The method according to claim 13, wherein said recombinant consensus interferon fusion protein is an Ig-consensus interferon fusion protein.

\* \* \* \* \*

UNITED STATES PATENT AND TRADEMARK OFFICE
CERTIFICATE OF CORRECTION

PATENT NO. : 7,674,453 B2
APPLICATION NO. : 10/503525
DATED : March 9, 2010
INVENTOR(S) : Giampiero De Luca It is certified that error appears in the above-identified patent and that said Letters Patent is hereby corrected as shown below:

Column 4,
Line 20, "In this antiviral assays" should read --In this antiviral assay--.

Column 7,
Line 19, "mTNF-alpha ip.." should read --mTNF-alpha ip.--.

Column 11,
Line 26, "activity a" should read --activity of a--.

Column 12,
Line 64, "liked to each other" should read --linked to each other--.

Column 13,
Lines 15-16, "80 000 IU/kg and 200 000" should read --80,000 IU/kg and 200,000--.
Line 37, "Feinberg et a.," should read --Feinberg et al.,--.

Column 14,
Line 47, "are is used" should read --is used--.

Column 15,
Line 17, "of less frequent" should read --or less frequent--.
Lines 50-51, "is not any way" should read --is not in any way--.
Line 62, "an range" should read --and range--.

Column 16,
Line 27, "Mycobaterium" should read --Mycobacterium--.
Line 47, "The i.v. route in was" should read --The i.v. route was--.
Line 51, "as vehicle" should read --as the vehicle--.
Lines 57-58, "by following criteria:" should read --by the following criteria:--.

Signed and Sealed this

Twenty-fifth Day of May, 2010

David J. Kappos
*Director of the United States Patent and Trademark Office*

Column 18,
Line 14, "diamonds).An" should read --diamonds). An--.

Column 19,
Line 57, "721 4" should read --721-4--.

Column 20,
Line 23, "(ion Gresser, Ed.)" should read --(Ion Gresser, Ed.)--.